United States Patent [19]

Mazza et al.

[11] Patent Number: 5,350,564
[45] Date of Patent: Sep. 27, 1994

[54] AUTOMATED CHEMICAL ANALYZER WITH APPARATUS AND METHOD FOR CONVEYING AND TEMPORARY STORAGE OF SAMPLE TUBES

[75] Inventors: John C. Mazza, El Toro; William A. Stark, Costa Mesa; Richard A. Scribner, Fullerton; Stephen L. Frye, El Toro; Kempton H. Hardiman, Mission Viejo, all of Calif.

[73] Assignee: Baxter Diagnostics Inc., Deerfield, Ill.

[21] Appl. No.: 83,733

[22] Filed: Jun. 28, 1993

[51] Int. Cl.⁵ .................... G01N 35/04; G01N 1/14
[52] U.S. Cl. .................... 422/63; 422/64; 422/65; 422/66; 422/67; 422/102; 422/104
[58] Field of Search ............ 422/65, 64, 67, 66, 422/102, 104, 63

[56] References Cited

U.S. PATENT DOCUMENTS

| | | | |
|---|---|---|---|
| 3,350,946 | 11/1967 | Isreeli | 73/864.91 |
| 3,533,744 | 10/1970 | Unger | 23/292 |
| 3,762,879 | 10/1973 | Moran | 23/259 |
| 3,832,135 | 8/1974 | Drozdowski et al. | 23/253 R |
| 3,883,308 | 5/1975 | Matte | 23/259 |
| 3,916,157 | 10/1975 | Roulette et al. | 235/61.12 R |
| 4,142,863 | 3/1979 | Covington et al. | 422/63 |
| 4,160,803 | 7/1979 | Potts | 422/101 |
| 4,224,032 | 9/1980 | Glover et al. | 23/230 |
| 4,234,540 | 11/1980 | Ginsberg et al. | 422/64 |
| 4,269,803 | 5/1981 | Jessop | 422/63 |
| 4,276,051 | 6/1981 | Ginsberg et al. | 23/230 R |
| 4,276,258 | 6/1981 | Ginsberg et al. | 422/64 |
| 4,296,070 | 10/1981 | Montalto et al. | 422/65 |
| 4,459,265 | 7/1984 | Berglund | 422/64 |
| 4,678,752 | 7/1987 | Thorne et al. | 435/291 |
| 4,849,176 | 7/1989 | Sakagami | 422/64 |
| 4,849,177 | 7/1989 | Jordan | 422/64 |
| 4,935,624 | 6/1990 | Henion et al. | 250/288 |
| 4,944,924 | 7/1990 | Mawhirt et al. | 422/104 |

Primary Examiner—James C. Housel
Assistant Examiner—Harold Y. Pyon
Attorney, Agent, or Firm—Mark J. Buonaiuto; Paul C. Flattery

[57] ABSTRACT

An automated chemical analyzer includes an automated conveyor apparatus for receiving a variety of sizes of test tubes, cuvettes, and sample tubes in a standard carrier member receivable into the analyzer. The standard carrier members may be interlocked in ranks and placed side by side in file to replicate the size and handling convenience of conventional test tube racks. However, the conveyor apparatus also provides for receipt of the carriers either as individuals for stat handling, or in interlocked ranks, or as rank and file groups for routine handling. The interlocked ranks of carriers are automatically unlocked from one another and fed along with the carriers having stat samples therein to a recirculating endless loop conveyor device which conveys the samples to at least one chemical analysis module, as well as providing a storage capacity both for samples in testing, and those samples awaiting verification of test results. Carriers with samples on which testing is completed and verified are discharged from the endless loop conveyor device into an off-loading facility which again interlocks the carriers and presents them in rank and file groups for subsequent handling like conventional test tube racks.

31 Claims, 9 Drawing Sheets

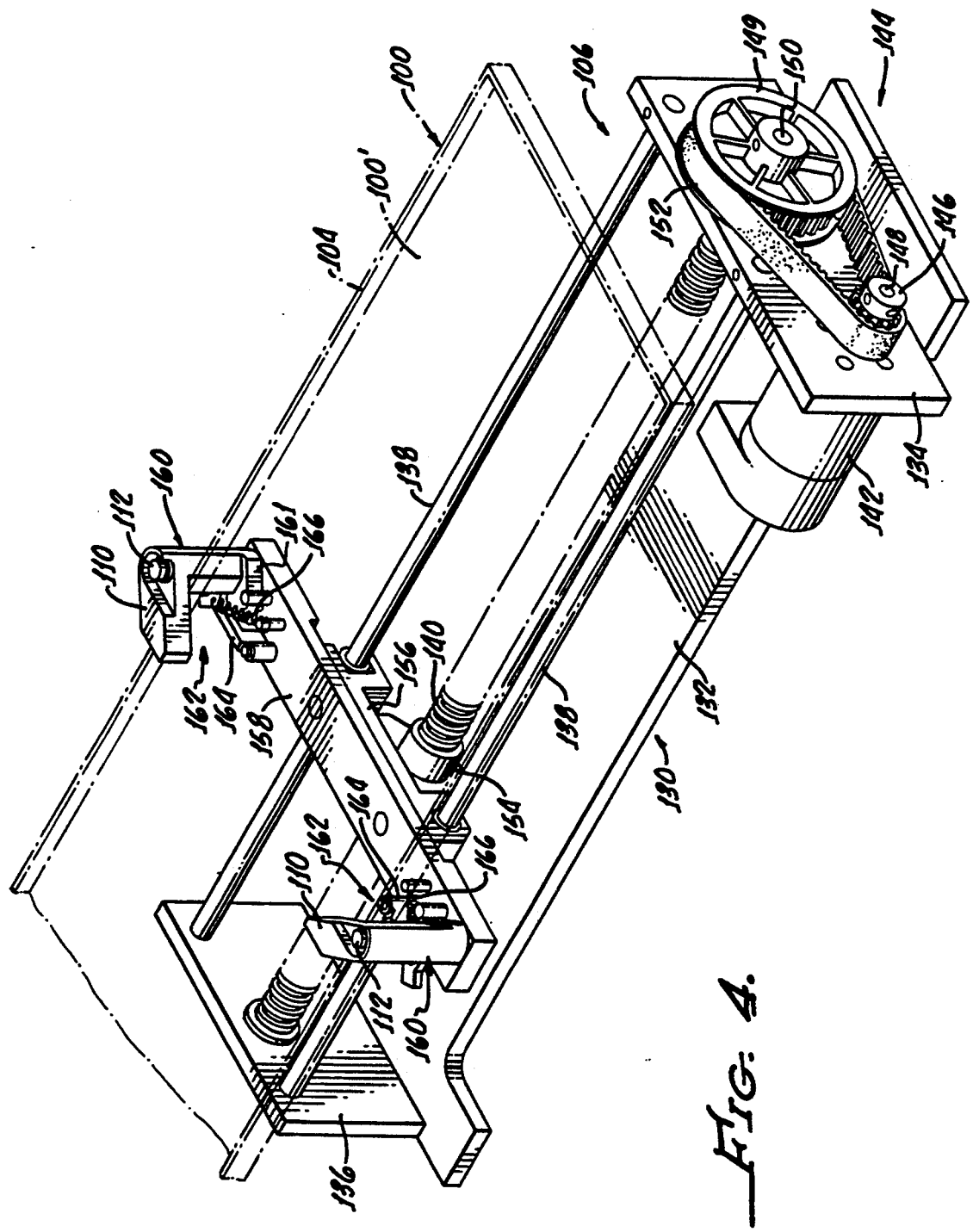

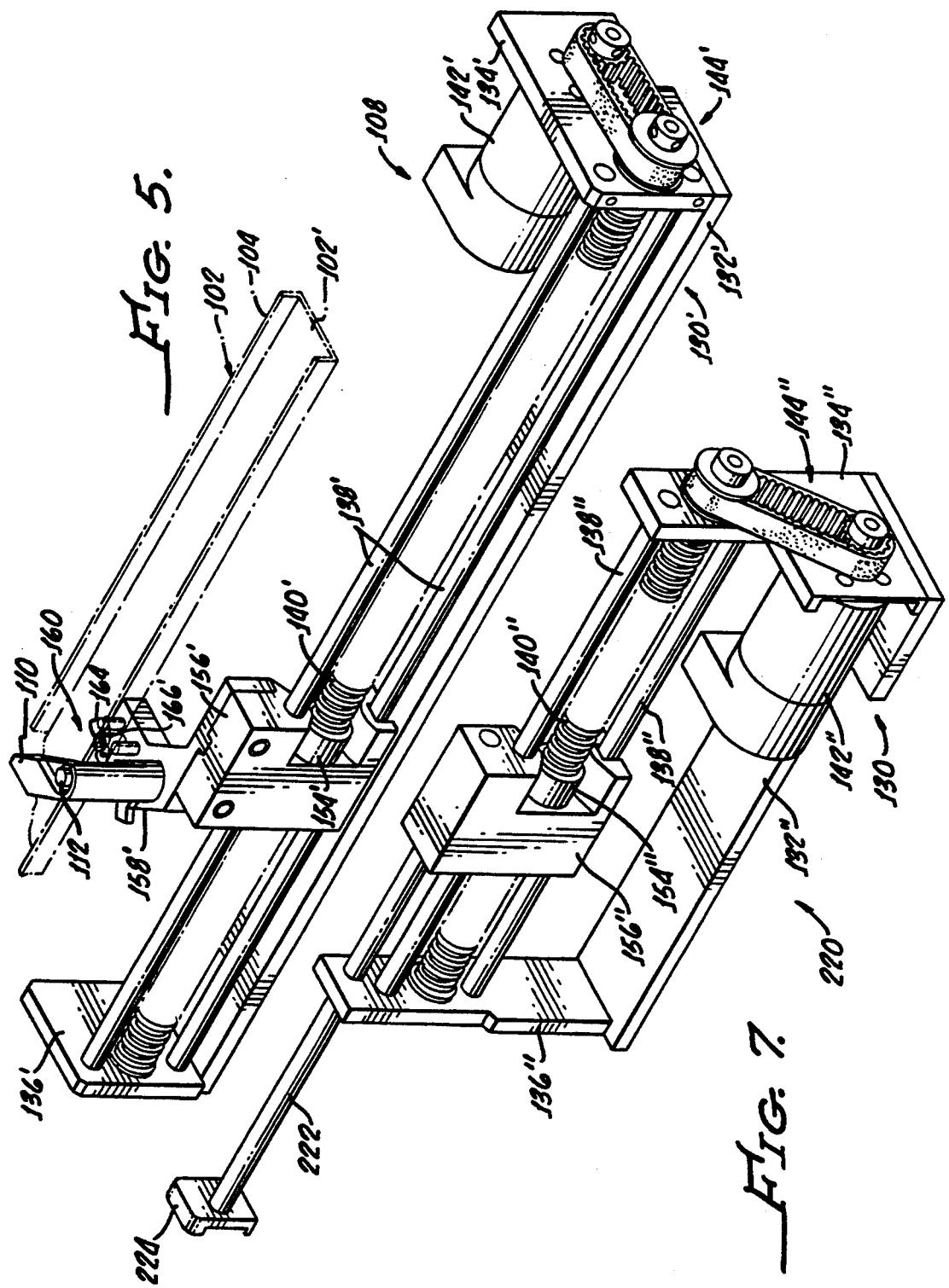

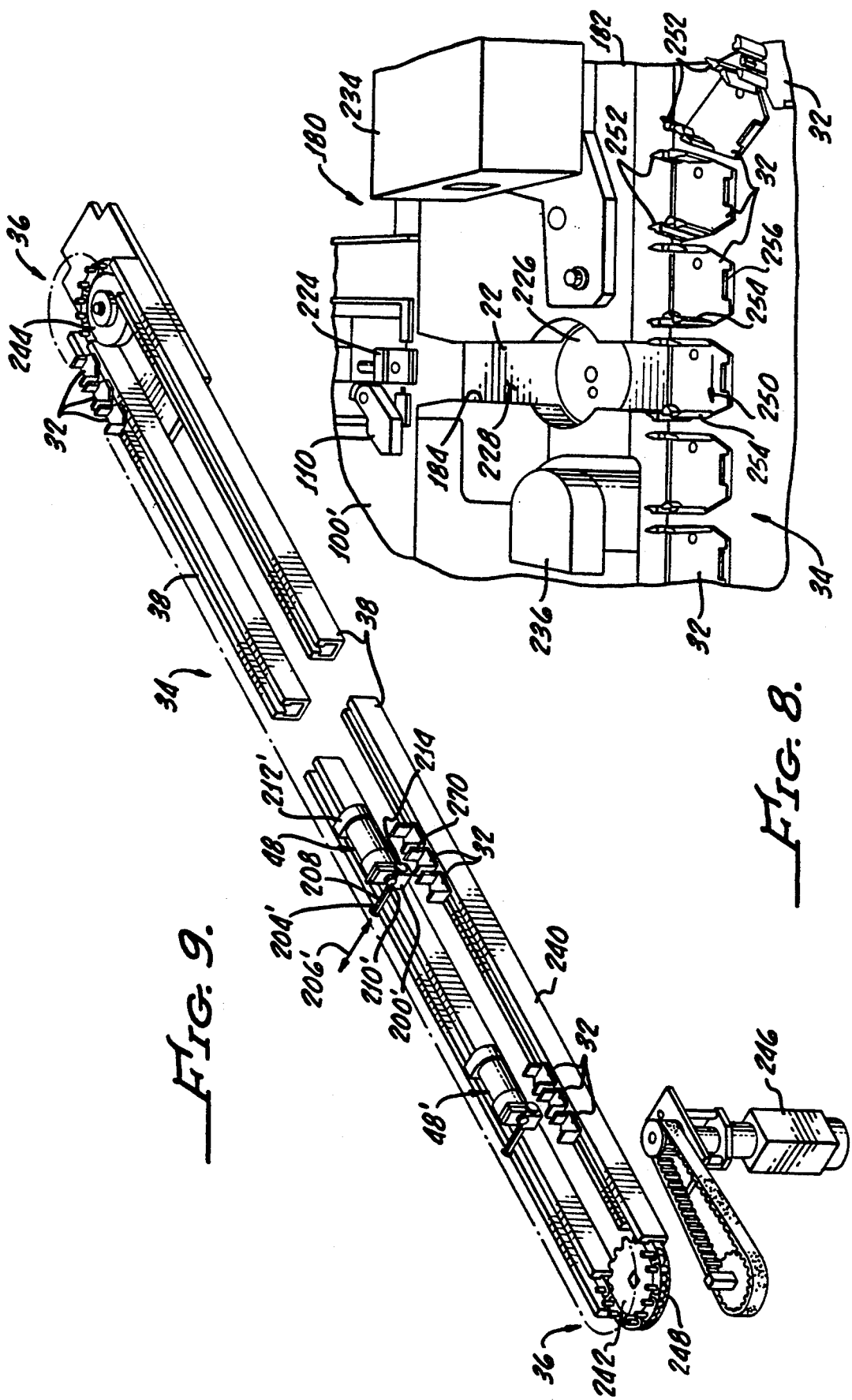

AUTOMATED CHEMICAL ANALYZER WITH APPARATUS AND METHOD FOR CONVEYING AND TEMPORARY STORAGE OF SAMPLE TUBES

CROSS REFERENCE TO RELATED APPLICATION

The present application relates to subject matter also the subject of U.S. patent application Ser. No. 07/906,257, filed on Jun. 29, 1992, and assigned to the same assignee as the present application.

FIELD OF THE INVENTION

The present invention relates to automated chemical analyzers, to conveyor systems and methods, to material handling devices and methods, and to temporary storage apparatus and methods. More particularly, the present invention relates to an adaptive, versatile conveyor system for feeding individual sample tubes, cells, cuvettes, and the like (hereinafter collectively referred to as "sample tubes") each held in an individual prismatic sample tube carrier, either from associated groups or batches which are taken in regular order, or from a stat sample area taken with priority; identifying the individual sample tubes; conveying and/or temporarily storing the individual sample tubes as required; transferring the individual sample tubes to and from one or more associated analysis modules of the apparatus as appropriate; retaining the individual sample tubes in temporary storage while test results are obtained, and returning the individual sample tubes to associated groups in response to an indication that analysis of a particular sample is complete and verified as reliable. The present invention has particular utility for use in automated chemical analyzers and related equipment for analysis and testing of blood, physiological fluids, and other biological samples.

BACKGROUND OF THE INVENTION

A wide variety of automated chemical analyzers are known in the art and are widely used in hospitals, clinics, and research laboratories. A particularly popular example of such a device is the multi-channel type of analyzer in which a series of different tests are performed simultaneously and in parallel with one another. The typical multi-channel analyzer generally utilizes liquid or solid reagents to react with a particular constituent present in a sample to result in a change in transmissibility, absorption, color, photo-optical characteristic or other coligative electrical or physical property of the sample. In conjunction with the multi-channel analyzer, a photo-optical system and electro chemical detector means are employed to determine the rate of reaction, or concentration of the constituent in the sample, and the like.

The usual method employed for performing these photometric procedures is to place a portion or aliquot of the sample solution in a small cell, tube, or cuvette provided with transparent walls, and then to interpose the sample solution between a light source and a photosensitive detecting element or to flow the sample past sensors. In order to perform multiple tests simultaneously on each sample most contemporary multi-channel analyzers utilize a number of small sample aliquots taken from a larger sample volume or specimen originally supplied to the machine. These larger sample specimens are stored and manipulated in cells or tubes of varying size and configuration, the most common being round elongate sample or test tubes, while others include rectangular or square cells and alternative configurations. This form of individualized sample processing avoids the problem of cross-contamination of samples which could occur with the earlier flow-through type of analyzers.

Although multi-channel automated analyzers have received wide acceptance, there are certain drawbacks associated with their use. For example, to provide precise and accurate handling of the sample tubes it is necessary to position and align the tubes within the apparatus accurately so that the various sample aliquots may be automatically and consistently removed as needed. Additionally, in order to correlate the multiple test results properly with the appropriate samples an accurate identification and tracking system must be utilized. As a result, a variety of specialized sample cells and identification means have been developed in the art. Unfortunately, the majority are machine-specific, which limits the applicability of the particular analyzer to those samples which are packaged in the specific sample tubes or cells. Alternatively, some analyzers provide for the use of adapters for sample cells other than the one machine-specific design, which adapters unfortunately, can be clumsy and time-consuming to use. Also, relatively highly-trained personnel are required to operate these conventional analysis machines effectively, as a mistake in their operation can render entire sample runs useless.

In order to handle the transportation, alignment, and tracking needs of large sample batches effectively, most prior art multi-channel analyzers utilize sample tube racks or carousels which are organized and loaded with sample tubes prior to positioning within the analyzer input area. Though these racks provide a degree of convenience in connection with sample tube handling, bulk storage, and identification, they make it virtually impossible to interrupt the analyzer apparatus once a sequence has been started and also impose a degree of restriction with respect to the handling of individual sample tubes. That is, the feeding of the sample tubes is sequential, as is the generation of test results to then be correlated with the particular sample tube, and to the patient from which the sample was taken.

Another significant disadvantage associated with these types of automated analyzing equipment is their inability to perform emergency, or "stat" tests. This inability arises because of the relatively long and complex setup times and the resultant inability to interrupt the order and flow of the organized samples of conventional analyzers. Similarly, though a relatively rare occurrence, if a sample tube should fracture or leak the entire sample run may be jeopardized if the machine cannot be interrupted without losing track of the samples in and in preparation for testing.

An alternative approach to sample tube handling has been the development of individual sample tube carriers which may be stored in racks and loaded into conveyor lines. For example, U.S. Pat. No. 3,916,157, issued Oct. 28, 1975, illustrates a specimen carrier for test tubes. The carrier is provided with a slotted base engageable with a geared conveyor track for transporting the carrier through an automated analyzer. Additionally, each carrier is provided with its own identification tag so that the sample in the carrier can be identified for tracking through the analyzer. An alternative sample container is disclosed in U.S. Pat. No. 3,350,946, issued Nov. 7, 1967. This system utilizes a vial with a vertical T-shaped flange that enables it to be inserted into a carousel. A machine-readable tag is attached to the vial for tracking purposes. Similarly, U.S. Pat. No. 4,944,924, issued Jul. 31, 1990, also discloses a test tube holder that pivots along a belt-like conveyor.

Still additional sample tube conveying and sample analyzing apparatus may be seen in U.S. Pat. No. 3,762,879, issued Oct. 2, 1973. In this device, sample tubes are manually inserted into a carousel, and sample aliquots are subsequently drawn from each sample tube for delivery to plural reaction tubes. The reaction tubes are carried in transversely aligned ranks on an elongate conveyor. In this analyzer, the sequential order of sample introduction and data generation would seem to rule out the introduction of stat samples, and breakage of a sample tube could cause possible loss of correlation of generated data to the particular samples.

An alternative sample analyzer which transposes the functions of conveyor and carousel is seen in U.S. Pat. No. 3,832,135, issued Aug. 27, 1974. In this apparatus, a conveyor is manually fed sample tubes, probably from a rack of the tubes. Subsequently, aliquots of each sample are withdrawn to be supplied to cuvettes carried on a carousel. The carousel has several concentric rows of test cells in which various tests are carried out on the aliquots of sample fluid. Sample handling appears to be entirely sequential so that stat samples cannot be taken with priority without interruption of the sequences already started.

A family of analyzers which combine a plurality of carousels is seen in U.S. Pat. Nos. 4,234,540, issued Nov. 18, 1980; and 4,276,051 and 4,276,258, both issued Nov. 18, 1980. In each of these devices, a sample carousel must be fed with sample tubes, so that aliquots may be withdrawn for depositing into reaction cells carried on a respective carousel. The reagents to be used in the reaction cells are carried in yet another carousel. Again trays of samples would appear to be necessary along with manual feeding of the sample cuvettes or tubes into the sample carousel.

Yet another analyzer which combines a carousel with a conveyor of sorts is seen in U.S. Pat. No. 4,459,265, issued Jul. 10, 1984. In this analyzer, the sample tubes are retained in trays, and the trays themselves are shuttled back and forth in a recess to align particular tubes with the aliquot withdrawal station. The reaction cells are carried at the perimeter of a carousel to receive both the aliquots of sample and reagents. Processing of stat samples would seem to require interruption of the test sequences already in process.

A more recent attempt to provide the combination of functions and advantages desired in an automated sample analyzer is seen in U.S. Pat. No. 4,678,752, issued Jul. 7, 1987. This analyzer provides a conveyor and a carousel, with the latter being employed as a short term storage area. A shuttle system is employed to move the samples between the introduction area, a liquid transfer station, a detector, and the storage area. The liquid sample and the reagents to be used therewith are carried as a package into and through the machine. The necessity to provide each sample to the analyzer along with the appropriate reagents would seem to require highly skilled operators for the machine, and the time sequencing of the samples in process to the single detector via the single shuttle would seem to limit the throughput of the analyzer. The sample and reagent packages also appear to be rather large so that the size growth of the machine with increasing number of samples thereon, or the limited number of samples in its processing inventory may be a disadvantage.

SUMMARY OF THE INVENTION

In view of the above, the present invention provides an apparatus and method for conveying and temporary storage of sample tubes to be fed to an analyzer. Preferably, the apparatus and method provides for the association of sample tubes in carriers which in rank and file arrangement generally replicate the size and handling characteristics of conventional test tube racks (i.e., a four by six rectangular array of test tubes, for example). Thus, the conventional sample carts and refrigerators used in hospitals and clinics need not be altered to permit samples to be collected from the patients in a format permitting expeditious processing through the conveyor apparatus of the present invention. The rank and file of samples, as well as individual stat samples, may be presented to the conveyor with little skill or special attention required. The conveyor feeds stat samples with priority immediately to an available analyzer, while rank and file samples are disassociated from one another, are individually identified, and are fed into the conveyor for transport to an analyzer. Samples received onto the conveyor from an analyzer are held until test results indicate the sample may be released, and are then fed from the conveyor into an off-loading area where the samples are again presented as associated rank and file groups for easy handling.

The conveyor apparatus according to a particularly preferred exemplary embodiment of the invention includes an on-loading area in the form of a tray whereat ranks of associated sample tube carriers may be slid into the machine. The sample tube carriers are preferably prismatic with a square section in plan view providing a lower sliding surface, which is slidably movable on the on-loading tray or other generally horizontal surfaces of the conveyor, for example. In elevation, the sample tube carriers are preferably rectangular with two pairs of opposed side surfaces. Each of the side surfaces defines a vertically extending slot opening to a central cavity of the carrier into which the sample tube is receivable. Thus, the sample tube and its contents may be viewed through the slots of the sample tube carrier.

Each of the opposed faces of the pairs of side surfaces of the sample tube carriers defines one respective part of a horizontally-extending tongue and groove feature. One of the pairs of opposed side surfaces defines an interlockable dove-tailed tongue and groove feature so that adjacent ones of the sample tube carriers may be linked or associated with one another by lateral sliding of the dove-tailed tongue and groove features together to form the associated ranks of carriers. The other opposed pair of side surfaces defines a respective one of a tongue and groove feature which is useful for indexing the sample tube carriers, and which may be interengaged for mutual support of adjacent ranks of the linked carriers. Each of the side surfaces of the carriers is unique, which facilitates rotational indexing of the sample carriers. Further, the linked carriers in ranks may be filed adjacent to one another to form mutually supportive rank and file arrangements of the carriers which emulate the conventional test tube racks now in common use.

At the on-loading tray of the apparatus, linked ranks of the carriers may be placed by relatively unskilled personnel in either of the two possible orientations. That is, adjacent ranks of carriers in file may be placed with the dove-tailed tongue and groove features oriented the same way so that the tongue and groove features of the other faces of the carriers nest together. Alternatively, adjacent filed ranks of carriers may have their dove-tailed tongue and groove features oriented oppositely so that the tongues or grooves of the tongue and groove features on the other faces of the carriers confront one another but do not nest together. As a result, when unskilled personnel load groups of carriers onto the conveyor, they need not be concerned with orientation of the groups other than to feed the interlocked carriers in rank orientation. The ranks of sample carriers are then automatically fed forwardly to an unlinking station, and are individually slid past sensors which determine the rotational orientation of the carrier by reference to the unique configurations of the tongue and groove features of the side surfaces.

Subsequently, the carriers are individually fed to a rotator assembly which provides both for the reading of a bar code tag on the sample tube in the carrier, and the rotational orientation of the carrier in a particular presentation. From the rotator, sample carriers are fed into individual receptacles of a bidirectional endless loop linear conveyor. This loop conveyor provides for transfer of the sample carriers to stations whereat each carrier is shuttled from its receptacle into an analyzer. Stat samples may be placed at the on-loading area into a respective que in any rotational orientation and are immediately fed into the rotator for delivery to the loop conveyor and to an analyzer.

Sample carriers returned from an analyzer to the loop conveyor are retained thereon, along with incoming samples en route to an analyzer, and priority stat samples which will be received by an analyzer prior to the rank and file samples, until the results of the tests on the sample are confirmed. Thus, the loop conveyor provides a dwell capacity in association with the analyzer. This dwell capacity also allows rank and file samples to be held in abeyance on the loop conveyor while stat samples traverse the conveyor immediately en route to the analyzer. In the event the test results are not confirmed, the particular sample may be fed from the loop conveyor back to the analyzer for a second or subsequent testing. Upon confirmation of the test results on a particular sample, that sample is brought by the loop conveyor to an off-loading station and removed from the loop conveyor receptacle. The off-loading station provides for association of the sample carriers in linked groups which are then filed adjacent to one another in rank and file presentation in an off-loading area. This presentation of the carriers and sample tubes provides once again for handling similarly to conventional test tube racks.

The entire operation of the conveyor is under the control of a dynamic controller so that each discreet action with respect to a sample carrier from the time its sample is identified until the sample test results are verified and the carrier is off loaded is tracked. Thus, test results are easily correlated with a particular sample and patient. Also, the location of each sample on the loop conveyor, and of vacant receptacles, which are available for receipt of a stat or of a rank and file sample, is always recorded. This feature of the conveyor along with its storage and dwell time feature makes possible the recall to an analyzer module of any particular sample in the event the results of a test are not verified as reliable. This latter feature is of high importance with stat samples. If the test results for any stat sample are not reliable, the sample will be recalled to the analyzer and retested. Only when the test results of each sample are verified will the sample be delivered to the off-loading area.

An advantage of the present invention is that it provides for handling of sample tubes in carriers much like conventional test tube racks are now handled. The rank and file samples may be loaded onto the conveyor by unskilled personnel, as no special training beyond a few minutes familiarization with the conveyor's operation is required. Stat samples can be fed to the conveyor in any orientation and will be taken onto the loop conveyor and fed to the analyzer module with priority. Stat samples do not interrupt the processing of samples already in test, as these tests continue. Nor do stat samples cause a loss of correlation of test results to particular samples because each sample is tracked individually whether it is a stat sample or a rank and file sample. The stat samples are simply taken onto the loop conveyor and transferred to the analyzer module with a conditional priority over the rank and file samples. The dwell time feature of the loop conveyor provides for the retention of both rank and file samples awaiting an opening on the analyzer and of tested samples awaiting verification of the reliability of test results.

Thus, when a test result is determined not to be reliable, the sample can be recalled to the analyzer for retesting. This latter feature is of particular importance with respect to the obtaining of reliable test results on stat samples, which may originate with a hospital emergency room or operating room, for example, so that test results are genuinely needed with urgency. When the test results of a particular sample are verified, the sample is released from the loop conveyor to an off-loading area of the conveyor. In this off-loading area, the sample carriers are again linked with one another in rank and file fashion to present the samples in groups familiar to hospital and clinic personnel. That is, the groups of samples may be arranged on carts and stored in refrigerators presently used for conventional test tube racks.

The above and additional advantages of the present invention will be apparent from a reading of the following detailed description of a particularly preferred embodiment of the invention taken in conjunction with the following drawing Figs., in which:

BRIEF DESCRIPTION OF THE DRAWING FIGURES

FIGS. 4 and 5 are perspective views at still larger size of respective portions of the conveyor apparatus seen in the preceding Figs.;

FIG. 7 is a perspective view rendered at a size comparable to that of FIGS. 4–6, of a portion of the conveyor apparatus seen in the preceding Figs.;

FIG. 8 is a fragmentary perspective view of the opposite side of the conveyor apparatus seen in FIG. 6, and including representation of its structural and functional cooperation with other parts of the conveyor apparatus seen in the preceding and subsequent Figs.;

FIG. 9 is a perspective view of an endless loop conveyor portion of the conveyor apparatus seen in the preceding Figs.

DETAILED DESCRIPTION OF A PREFERRED EMBODIMENT OF THE INVENTION

An Overview

Figure 1:
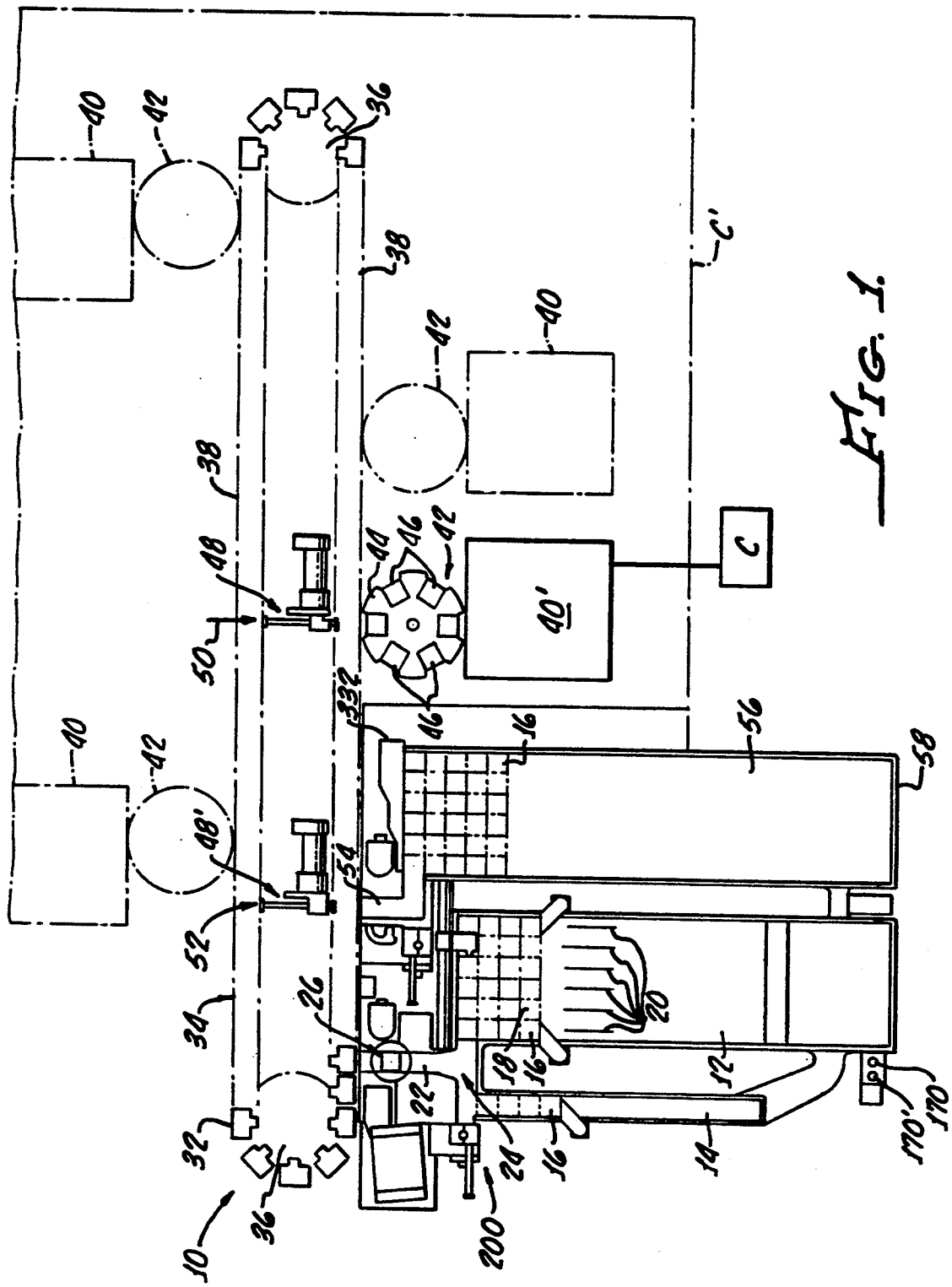
FIG. 1 is a plan view of an automated chemical analyzer including a conveyor apparatus embodying the present invention in association with several chemical analysis devices served by the conveyor.

Viewing FIG. 1 in order to gain a generalized understanding of a chemical analyzer 8 with a conveyor apparatus embodying the present invention, the conveyor 10 includes an on-loading area generally referenced with the numeral 12, and including a stat on-loading line or que, referenced with the numeral 14. Slidably received into the stat on-loading line is a plurality of individual lined up sample tube carriers, which are square in plan view, and are referenced with the numeral 16. A plurality of like sample tube carriers are also seen on the general on-loading area. These sample tube carriers 16 on the general on-loading area are slidably received also and are arranged in interlocked lateral ranks, extending along the line indicated with the numeral 18. As can be seen viewing FIG. 1, plural interlocked ranks 18 of sample tube carriers are arranged one behind the other so that individual sample tube carriers in the ranks align to form forwardly-extending files referenced with the numeral 20. Consequently, the sample tube carriers 16 on the general on-loading area 12 are arranged in rank and file with a rectangular grid pattern.

As will be described in greater detail below, the on-loading area 12 includes provision for slidably advancing the sample tube carriers 16; for laterally sliding the carriers out of their que 14 of the stat line, or out of files 20, and into alignment with a loading chute, referenced with the numeral 22; for slidably advancing the carriers individually along the loading chute 22, which includes sensors 24 for determining the rotational orientation of each sample tube carrier 16, and which advancement also has the effect of unlocking the individual carriers 16 from their ranks 18; for sliding the individual carriers 16 onto a rotator assembly 26 which forms a portion of the floor of the loading chute 22 whereon the sample tube carrier 16 and sample tube 28 therein is rotated so that a bar code tag 30 (best seen viewing FIGS. 2A and 2B) on each sample tube can be read to identify each individual sample, and the rotational orientation of each sample carrier is brought to a preferred presentation; and for slidably advancing the individual sample tube carriers 16 further along the loading chute 22 and into an individual aligned receptacle 32 of a plurality of similar receptacles on an elongate endless loop conveyor 34.

The receptacles 32 of loop conveyor 34 extend upwardly, have a floor portion aligning with the floor of loading chute 22, and are carried on a multi-link flexible chain portion of the conveyor 34, which chain portion is not visible in FIG. 1, but is described in greater detail below. Thus, the on-loading area 12 and stat que 14 may be viewed as parts of a U-shaped on-loading area (albeit, an inverted U-shape as seen in FIG. 1), with these features defining the uprights of the U-shape, and the lateral motion of the carriers 16 from each of these features defining the horizontal cross bar of the U-shape. The loading chute 22 extends toward the loop conveyor 34 from the cross bar of the U-shaped loading area just described.

The endless loop conveyor 34 includes a pair of end turns, each generally referenced with the numeral 36, and a pair of elongate runs, each referenced with the numeral 38. Along each side of the conveyor 34, along side of the runs 38 thereof, is situated a plurality of analyzer modules, each referenced with the numeral 40. Because each of the analyzer modules 40 is in some respects the same so far as its interface with the conveyor 10 is concerned, and the analyzer modules 40 themselves are contextual with respect to the present invention, only the one analyzer module 40' is described in any detail herein, the other analyzer modules 40 being understood as possibly variable in their function, but each interfacing in the same way with the conveyor 10.

The analyzer module 40' includes a small transfer and storage carousel 42. The carousel 42 includes a turntable 44 with six peripheral receptacles 46 each having a floor portion at the level of the floor portion of the receptacles 32 on the loop conveyor 34, while the turn table 44 is rotational in discreet steps of one-sixth revolution. One of the receptacles 46 at the perimeter of the turntable 44 thus aligns perpendicularly with the run 38 of conveyor 34. The loop conveyor 34 can be stopped with one of the receptacles 32 aligned with one of the receptacles 46. That is, when the loop conveyor 34 is stopped with one of the receptacles 32 aligned with the loading chute 22, the location of each analyzer module 40 along the endless loop of conveyor 34 is such that a receptacle 32 aligns with a receptacle 46 of each one of the transfer carousels 42 of the analyzer modules 40. Consequently, simultaneous transfers of sample carriers 16 between the loop conveyor 34 and any of the analyzer modules 40 may take place at the same time that a sample carrier is inserted into the loop conveyor 34 at loading chute 22.

In order to transfer the sample carrier 16 from the loop conveyor 34 to the aligned receptacle 46 of the turntable 44, the conveyor 10 includes a transfer ram assembly, referenced with the numeral 48 still viewing FIG. 1. While the transfer ram assembly 48 is described in greater detail below, it is sufficient at the present time to appreciate that the transfer ram assembly 48 includes an extensible ram engageable with the sample carrier in the aligned receptacle 32, as is depicted by arrow 50 viewing FIG. 1, to slide the sample carrier 16 from receptacle 32 into receptacle 46. Alternatively, the analyzer 40 includes a respective transfer ram assembly (not visible in the Figs.) for sliding the sample tube carriers 16 back onto the conveyor 34 when a receptacle 32 stops in alignment with the carousel 42. Extension and retraction of the rams of the transfer ram assembly 48, and of the similar ram assembly of the analyzer module 40, is coordinated with the movement of the loop conveyor 34 so that transfers of sample carriers only take place when the loop conveyor 34 is stopped with the receptacles 32 in alignment with receptacles 46, and the loop conveyor cannot move while the rams are advanced.

At the analyzer modules 40, the samples of fluid or other physiological material in the sample tubes 30 is subjected to chemical or other analysis. Those ordinarily skilled in the pertinent art will recognize that this chemical or other analysis may require from as little as a few seconds to as long as several minutes or longer for each sample tested. Also some tests may require the addition or reagents or the making of observations at certain scheduled times after the commencement of a test. These observations will ordinarily be made by a photometric device which is part of the analysis module 40. Thus, some of the tests may require that the sample or a portion thereof be presented to the photometric device several times at scheduled intervals so that the test results may include consideration of not only the completed results of a chemical reaction, for example, but also determination of the rate at which the reaction progresses toward completion.

Consequently, the analyzer modules 40 may retain some samples on the respective carousels 42 for the entire duration of particular tests, while other tests will permit return of the sample to the conveyor 34, with one or more subsequent recalls of the sample to the analyzer module via the carousel 42. This type of testing sequence allows the analyzer to accept other samples onto the respective carousel and to begin or complete tests on these samples while necessary time is allowed to pass for sample testing sequences started earlier. Thus, a time management and analyzer capacity and availability scheduling function is carried out by utilization of a combination of the storage capacity of the plural receptacles 32 on loop conveyor 34, and the smaller storage capacity of the transfer carousels 42 of each analyzer module 40. Upon completion of each test sequence for a particular sample at an analyzer module, the sample is transferred back to the loop conveyor for conveying to another one of the analyzer modules, or for a waiting period during which test results are verifies, as is explained below.

Further to the above, once the steps of each analysis has been completed on a particular sample, the results of the analysis must preferably be compared to other test results on the sample and to established norms in order to determine whether the test results are reliable. That is, if some particular part of the test results are aberrant, either by comparison to norms or to other parts of the test results on that sample, for example, then the test results will not have a high confidence factor. The loop conveyor 34 offers sufficient storage capacity that the samples may be retained on the conveyor and may circulate thereon with incoming samples and other samples in various stages of testing, while the test results for each particular sample are compared with comparison standards and rules. If the sample test results are reliable, the sample is off-loaded, as explained below. On the other hand, if the test results for a particular sample do not appear to be reliable, the sample can be retested, and this retesting can be carried out on a priority basis if the sample was identified as a stat sample by its introduction to the loop conveyor via the stat line 14. In either case, whether the sample is a rank and file sample or a stat sample, it can be recalled from the conveyor 34, and all or particular ones of the scheduled tests for that sample will be repeated.

Once a sample has been released from the possible necessity for further testing, the sample is brought by the loop conveyor 34 to an off-loading station 52. This off-loading station, like the analyzers 40, is aligned with one of the stopping locations for the receptacles 32 so that on-loading and transfers to the analyzers 40 may occur simultaneously with the off loading operation at station 52. The conveyor 10 includes another transfer ram assembly 48', like the assembly 48, but aligned with an L-shaped off-loading chute portion 54 of the station 52. As will be further explained below, the off-loading chute 54 includes associated apparatus and features for interlocking the sample carriers 16 in like laterally extending ranks each including a selected number of carriers and extending onto an off-loading tray 56, and for subsequently arranging the ranks of interlocked carriers adjacent one another so that the carriers are once again in rank and file presentation on the tray 56. The rank and file of carriers on the off-loading tray 56 are automatically advanced toward the free end 58 of the tray, there to once again be conveniently handled for storage or disposal by comparatively unskilled personnel.

In order to control and coordinate the several functions of the conveyor 10, a controller generally referenced on FIG. 1 with the character "C" is provided. The controller "C" is described in greater detail below, but should be recalled as the sequencing, sample tracking, and decision making function in connection with the following more particularly described aspects of the conveyor 10. Preferably, the controller "C" is also interfaced with each analysis module 40 via a data bus, which is indicated with the dashed line C' on FIG. 1. This data bus interface allows the controller "C" to receive test results for particular samples from the analysis modules so that these results can be verified as described, or to receive indications that a particular sample may be released from the loop conveyor 34, for example.

The Sample Tube Carriers

Figure 2A:
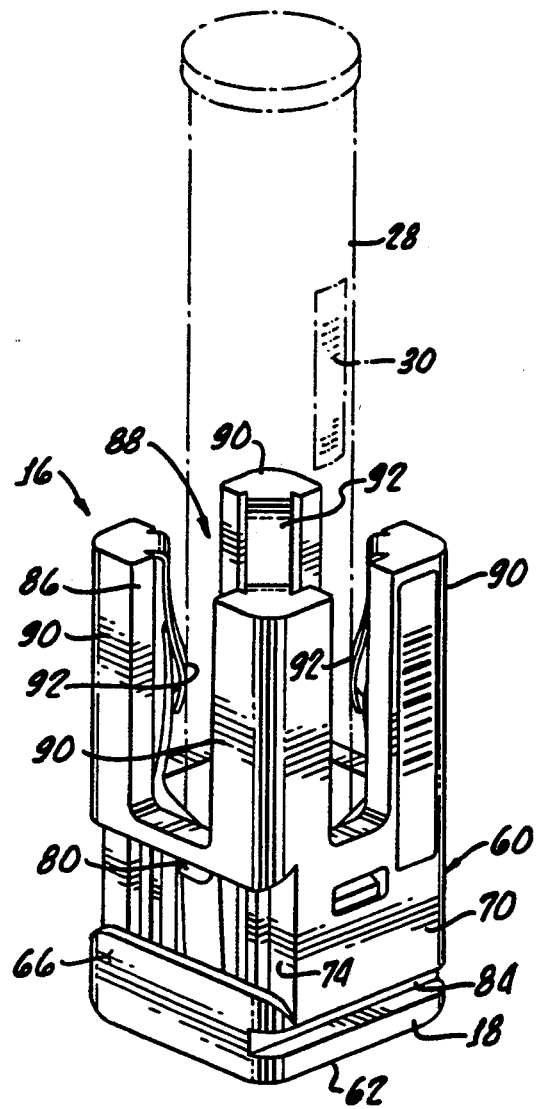
FIGS. 2A and 2B are opposite perspective views of a sample tube carrier particularly adapted for use in the automated chemical analyzer and associated conveyor apparatus of the present invention, as seen in FIG. 1.
Figure 2B:
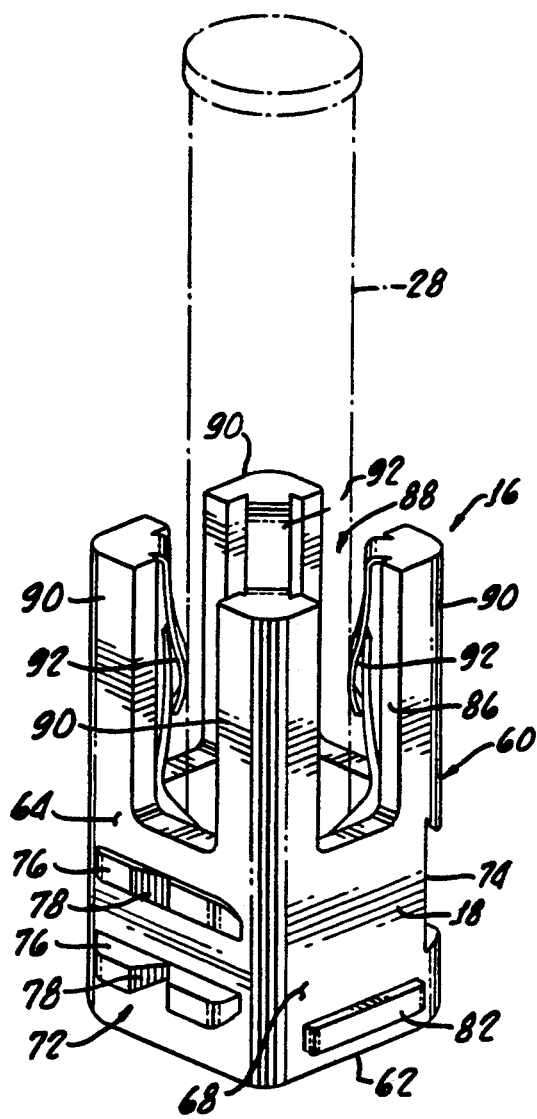

Viewing now FIGS. 2A and 2B in conjunction, a representative one of the sample tube carriers 16 is depicted in perspective. The carrier 16 includes a prismatic body, generally referenced with the numeral 60. The body 60 is generally square in plan view, and defines a lower sliding surface 62. Body 60 also defines two pairs of opposed vertical side surfaces 64,66, and 68,70. The one pair of side surfaces 64,66 define respective ones of a horizontally-extending mutually engageable dove-tail tongue and groove feature 72,74. That is, the side surface 64 defines a pair of vertically spaced apart and divergently angulated (that is, cooperatively dove-tailed) projections 76 cooperatively defining a dove-tailed tongue 72, while the side surface 66 has a matching dove-tail groove 74. At both the upper and lower projection 76, a vertically extending notch 78 transects the projection. Cooperatively, at groove 74 near the upper extent thereof, an outwardly extending resiliently yieldable detent member 80 extends into the groove 74 in alignment with the level of the upper projection 76. Thus, adjacent carriers 16 may be interlocked with one another by sliding the tongue feature 72 into the matching groove feature 74 of the adjacent carrier. The detent member 80 is received into the notch 78 of the upper projection 76 to removably retain the carriers 16 in interlocked alignment. This interlocking of adjacent carriers 16 form ranks of such carriers, as was referred to above.

Similarly, the other pair of side surfaces 68,70, define respective ones of a horizontally-extending mutually engageable tongue and groove feature 82,84. The tongue and groove features 82,84 do not interlock like the features 72,74, and do not require lateral relative sliding motion of adjacent carriers 16 to interengage. That is, simply moving adjacent carriers 16 into abutting engagement with one another at their respective surfaces 68,70 will engage the features 82,84 so that adjacent carriers offer vertical support to one another. Thus, groups of the carriers in ranks may be placed adjacent to one another with the tongue and groove features 82,84 of adjacent ranks interengaged, and may then be picked up and handled much like a conventional test tube tray.

Also, consideration of the above will make clear that each side surface 64,66,68,and 70 of the carriers 16 is unique. That is, the rotational orientation of the carriers can be determined by sensing whether a tongue or a groove is presented on a particular face of the carrier, and whether the tongue or groove is dove-tailed.

Further consideration of the FIGS. 2A and 2B will reveal that each side surface 64–70 defines a respective vertically extending slot 86 opening to a central cavity 88 of the carrier. Because the slots 86 align with one another, and the sample tubes 28 have transparent walls, the contents of the sample tubes may be viewed through the slots 86 so that color changes may be observed, for example, and light beams or other radiation may be directed through the sample for diffraction analysis, for example. Similarly, if bar code tag 30 is positioned below the top of carrier 16 it can be read through one of slots 86. The central cavity 88 is surrounded by four corner post portions 90 of the body 60, which portions cooperatively define the slots 86. From each corner post portion a centering spring 92 extends toward the center of the cavity 88. Immediately below the level of the slots 86, the cavity 88 terminates in a central downwardly extending conical recess (not visible in the drawing Figs.). The sample tube 28 which is received into the cavity 88 is engaged by the centering springs 92, and seats in the conical recess to be centered in the cavity 88. Because of the resilience of the centering springs 92, a variety of sizes of sample tubes may be carried in the carrier 16. For example, the carrier 16 may accept and center sample tubes of from about 10 mm to about 17 mm outside diameter. Also, sample tubes from about 50 mm to about 110 mm in length may be carried in the carriers 16. Also, the bar code identification tag 30 may be viewed through the slots 86 if the tag happens to be placed on the sample tube below the level of the corner posts 90.

Alternatively, the sample carriers 16 may be provided with other means by which they may releasably associate in a mutually supportive relationship with one another. Without limitation, an example of such alternative structure for associating the sample carriers 16 with one another would be to embed magnetic material or permanent magnets flush in the side surfaces 62, 66, and 68, 70 of the sample carrier 16, either with or without the presence of dove tail tongue and groove features. If the sample carrier 16 are simply provided with matching tongue and groove features which are not dove tailed, but permanent magnets and juxtaposed bodier of magnetic material are embedded in the side surfaces such that selected side surfaces will supportingly engage one another, via their engaging tongue and groove features, and are maintained magnetically in engagement, then the carriers 16 will mutually support one another and releasably interlink.

Still alternatively, rather than using tongue and groove features on the side surfaces 62–70, plural v-shaped situations might be used. Another alternative configuration for the carriers 16 is to configure the side surfaces 62–70 like bristle blocks, with plural outwardly extending stems which will interlock with the stems of an adjacent carrier member in a preferred orientation. By providing the bristle block stems in differing sizes or arrangements on the perpendicular faces of the carrier members 16, these carriers can be limited to interlocking with one another in a preferred relative orientation.

On-Loading Apparatus and Method

Figure 3A:
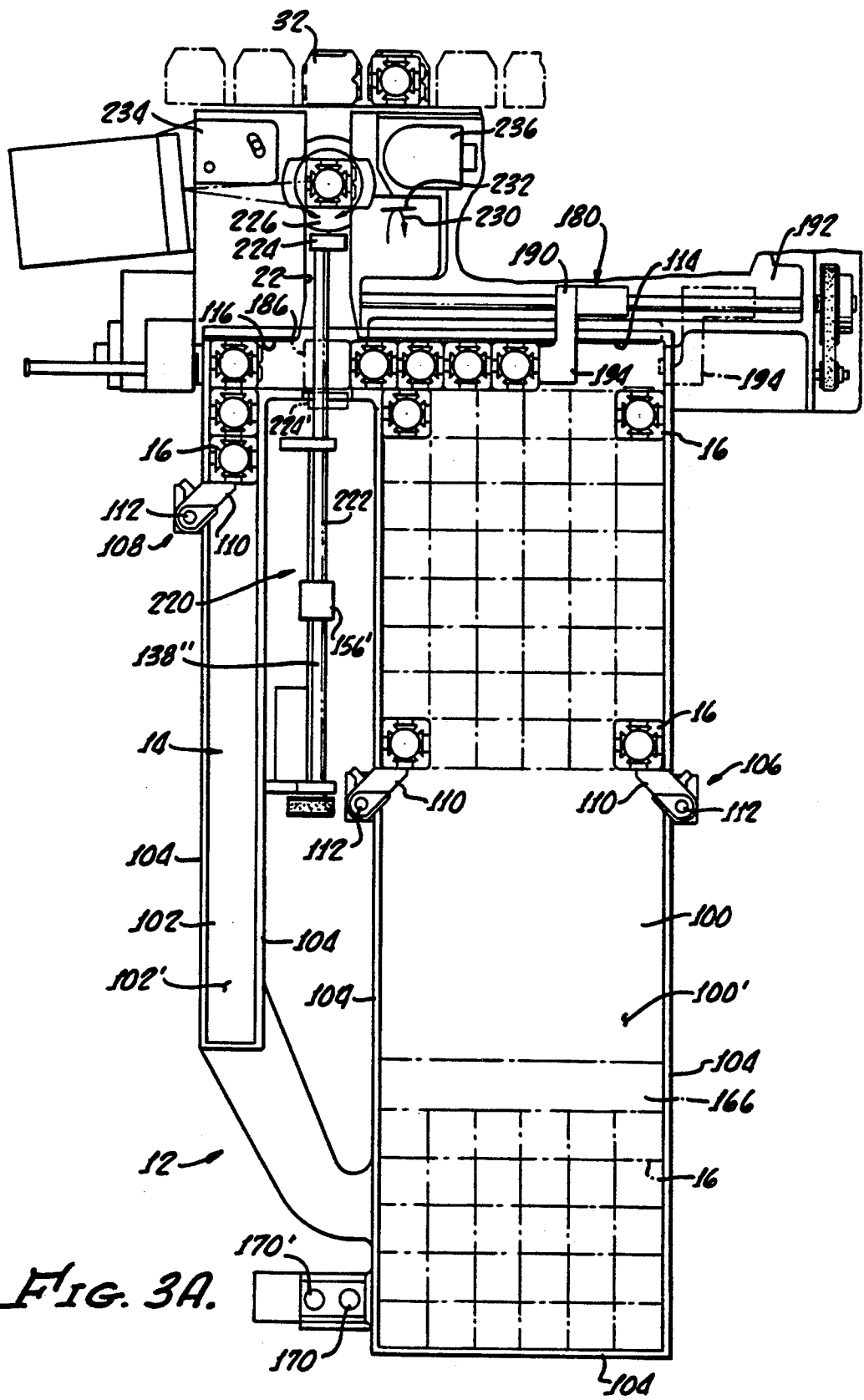
FIGS. 3A and 3B are adjacent parts of a fragmentary view of FIG. 1, presented in greater detail at a considerably enlarged size.
Figure 3B:
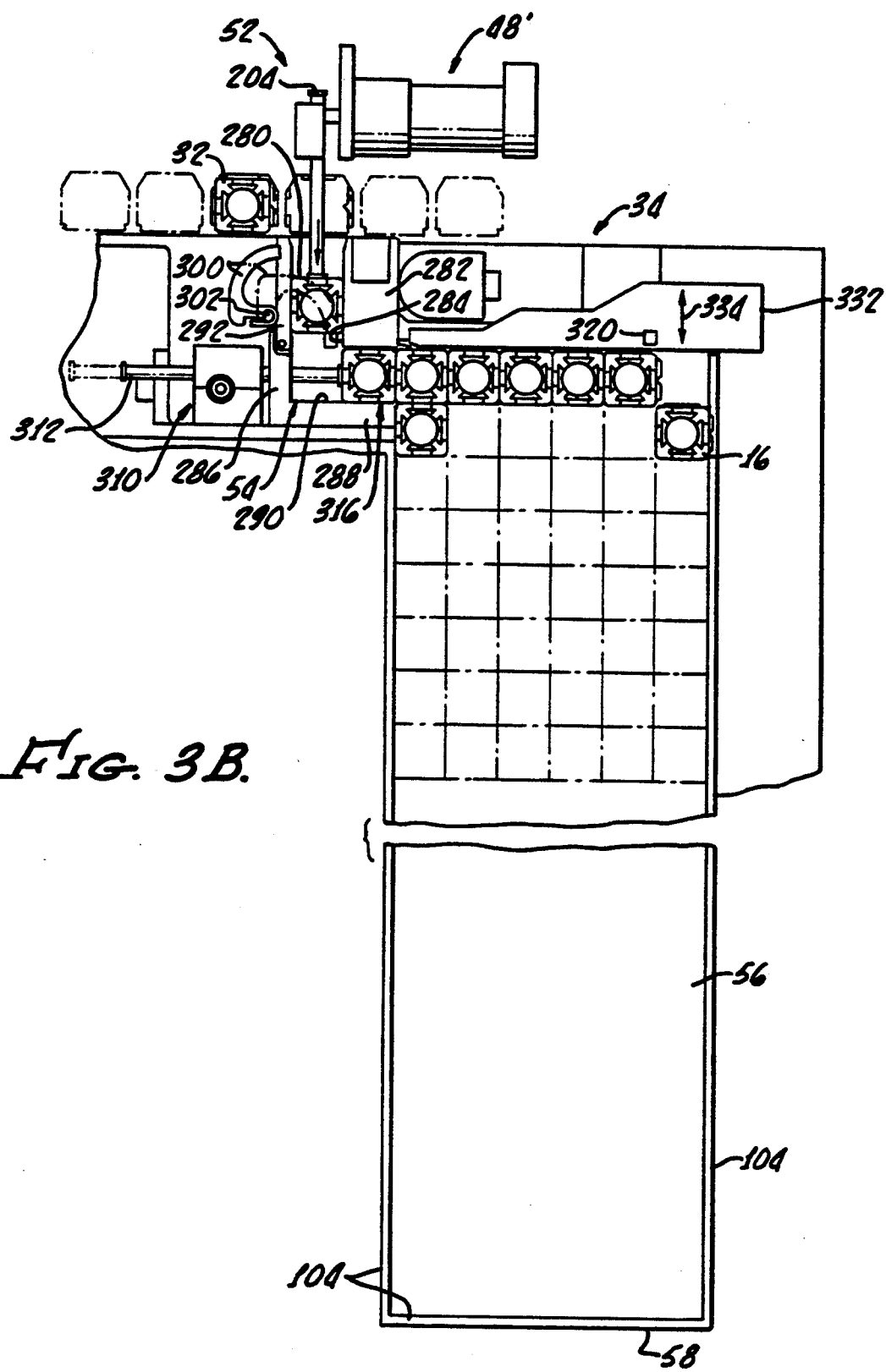

Viewing now FIGS. 3A and 3B, which are adjacent parts of the same view and are hereinafter collectively referred to as FIG. 3, the on-loading area 12 of the conveyor 10 is depicted in greater detail. The on-loading area 12 includes a pair of suspended elongate horizontal trays 100,102, which respectively form the sliding surfaces 100', 102' for the rank and file carriers 16 in the on-loading area 12, and for the sample carriers 16 in the stat que 14, as described above. That is, the lower sliding surface 62 of the sample carriers 16 slidably engages the upper surfaces 100', 102' of the trays 100,102. The trays 100,102 each have upturned side edges or associated edge walls, generally referenced with the numeral 104 so that the sliding surfaces 100', 102' of the trays are bounded and sample carriers 16 can not slide off the sides or ends of the trays.

In order to advance sample carriers placed on the trays 100,102 toward the loop conveyor 34, each tray 100,102 has disposed below it and associated with it a respective advancer assembly 106,108, seen in FIGS. 4 and 5, respectively. Each advancer assembly 106,108 includes a pivotal drive dog 110, a pair of such drive dogs are included on the advancer 106, and a single drive dog 110 in the case of the stat advancer 108. These drive dogs 110 are pivotal about a respective drive pin 112 so that retracting movement of the dogs past ranks or individual carriers 16 on the trays 100,102 causes the dogs to ratchet past the carriers. On the other hand, once past the carriers 16, advancing movement of the dogs 110 causes them to engage and move the carriers 16 forwardly into engagement with respective abutment walls 114,116 (seen in FIGS. 3 and 6) at the front of the rank and file on-load area 12, and stat que 14. The advancer assemblies 106,108 are disposed below the respective trays 100,102 so that in FIG. 3 only the drive dogs 110 are visible.

Turning to FIG. 4, the rank and file advancer assembly 106 is seen to include an elongate frame, generally referenced with the numeral 130. Frame 130 includes an elongate base plate member 132, which is spaced below and parallel with the tray 100. At respective ends of the base plate 132, a pair of upright spaced apart end plates 134,136 are secured by threaded fasteners (not seen in the drawing Figs.). Extending between the end plates 134,136 is a mutually parallel pair of slide shafts, each referenced with the numeral 138. Disposed between the pair of slide shafts 138, and journaled by the end plates 134,136, which also constrain its axial movement, is a lead screw 140. A servo motor 142 is also carried by the one end plate 134. A drive assembly, generally referenced with the numeral 144 connects the servo motor drivingly to the lead screw 140. This drive assembly 144 includes a driving sprocket 146 on a drive shaft 148 of the motor 142, and a driven sprocket 149 connected drivingly to the lead screw 140 at an end portion 150 thereof. A toothed timing belt 152 extends between and engages the sprockets to provide a positive slip-free driving connection between the servo motor 142 and the lead screw 140.

Threadably engaging the lead screw 140 is a nut member 154 which is carried by a slide block 156. The slide block 156 is slidably carried on the slide shafts 138, and in turn carries an elongate laterally extending mounting plate 158. Near the ends of the mounting plate 158, the drive pins 112 are carried, and extend upwardly on each side of the overlying tray 110, as is depicted in phantom lines on FIG. 4. Pivotally received on the drive pins 112 are respective drive dog members 160. At their upper ends, the drive dog members 160 define as a portion thereof the drive dogs 110, seen in FIG. 3. Below the drive dog portions, the drive dog members 160 include a flange portion 161 adjacent the mounting plate 158, and with which a biasing assembly 162 cooperates. This biasing assembly 162 includes a biasing arm 164 cooperating with the drive dog member 160, under the action of a coil spring 166 to pivotally bias the drive dog portions 110 toward the carriers 16 which are carried on the overlying tray 100.

When a group of carriers 16 is placed on the tray 100, whether this group includes a single rank of carriers 16, or a rank and file grouping including, for example, twenty-four carriers (i.e., four ranks each of six carriers 16, arranged one behind the other), the human operator of the conveyor 10 moves the group forwardly of a no-load zone (or staging area) 168, and presses a momentary contact switch, the push button 170 for which is seen in FIG. 3. This contact closure input to the controller of the conveyor 10 causes the servo motor 142 to rotate in a first direction retracting the drive dogs 110. That is, the drive dogs 110 move in the direction of arrow 170, viewing FIG. 3. With this movement, the drive dogs 110 ratchet past the carriers 16, which the human operator has just set upon the tray 100, until they reach the no-load area 168. Upon the drive dogs 110 reaching the no-load area 168, the direction of rotation of servo motor 142 is reversed to cause the drive dogs 110 to advance toward abutment wall 114, viewing FIG. 3. The drive dogs 110 catch the group of carriers 16 just placed on the tray 100 and advance the carriers either against the abutment wall 114, or against the other carriers 16 already on the tray 100, until a predetermined resistance to further movement is sensed at servo motor 142. This predetermined resistance to further forward movement of the drive dogs causes servo motor 142 to shut off until a subsequent event (to be further described below) causes either a further advance of one carrier spacer or a retraction and subsequent advance as just described to pick up additional new carriers 16 just placed on the tray 100 by the human attendant.

Turning now to FIG. 5, it will be seen that the advancer assembly 108 for the stat que 14 has many structures and features in common with the advancer 106. Consequently, features of the advancer 108 which are analogous in structure or function to those already described with reference to advancer assembly 106 and to FIG. 3 are referenced on FIG. 4 with the same numeral used previously, and having a prime added thereto. The advancer assembly 108 includes a frame 130', with base plate 132', carrying a pair of end plates 134', 136'. Between the end plates 134', 136', extends a pair of slide shafts 138', and a lead screw 140', which is journaled by the end plates 134', 136'. The end plate 134', carries a servo motor 142' coupled in driving relation with the lead screw by a drive assembly 144'. A nut member 154', is threadably engaged by the lead screw 140', is carried by a slide block member 156', and carries a mounting plate 158'. On the mounting plate 158' is carried a drive pin 112 pivotally carrying a drive dog member 160' with a drive dog portion 110 visible in FIG. 3. A biasing arm 164' is pivotally carried on the mounting plate, and is acted on by a coil spring 166' to yieldably urge the drive dog portion 110 of the drive dog member 160' toward the carriers 16 seen in the stat que 14 of FIG. 3. Similarly to the operation of the rank and file advancer 106 described above, the stat advancer 108 is under the control of a push button switch 170' seen in FIG. 3 to retract the drive dog 110 behind stat samples placed in the que 14, with subsequent advance of the drive dog 110 and sample carriers 16 toward the abutment wall 116.

Viewing FIG. 3 once again, it will be seen that when a rank of interlocked sample carriers 16 in the on-loading area 12 is against abutment wall 114, or a single sample carrier 16 in stat que 14 is against abutment wall 116, these sample carriers must be moved laterally so that they will individually align with the loading chute 22. In order to align the sample carriers 116 with loading chute 22, as well as to perform other functions which will be explained also, the conveyor 10 includes an actuator assembly, generally referenced with the numeral 180, and seen in FIG. 3, but best seen in FIG. 6. The actuator assembly 180 includes a housing 182 which defines the abutment wall surfaces 114, 116, and also defines a forwardly extending groove 184 which defines the loading chute 22, as will be explained in greater detail below.

In order to move the rank and file samples leftwardly, viewing FIG. 3, from their position in alignment with the tray 100 to a position referenced with numeral 186 in alignment with the chute 22, actuator assembly 180 includes a lateral advancer assembly, generally referenced with the numeral 188. Because of its similarity with the advancer assemblies described earlier with reference to FIGS. 4 and 5, the lateral advancer assembly 188 is not described in detail other than to point our that an upwardly extending portion 190 of a slide block of the lateral advancer assembly extends upwardly through a slot 192 immediately behind the abutment wall surface 114, and carries a pusher member 194 extending toward the viewer of FIG. 6 to engage the right-hand end of the first rank of carriers 16 in engagement with the surface 114. This pusher member 194 moves leftwardly, viewing FIG. 6, or toward the referenced position 186, viewing FIG. 3, in incremental steps of lateral advancement to bring successive ones of carriers 16 from tray 100 to the referenced position in alignment with the loading chute 22. When the last carrier member 16 of a rank is advanced to the reference position 186, the pusher member 194 is retracted in one motion to the far side of the tray 100, as is seen in phantom lines on FIG. 3.

Alternatively, in the event there is a stat sample carrier 16 in the que 14 on tray 102, the actuator assembly 180 includes a rack-and-pinion type of lateral advancer, which is generally referenced with the numeral 200, to move the sample carrier to the reference position 186 as soon as this reference position is vacated, as will be explained. The lateral advancer assembly 200 includes a guide block 202 in which a ram member 204 is reciprocably movable, as is indicated by arrow 206. The ram member 204 defines a rack of gear teeth 208 which are engaged by a pinion gear 210. This pinion gear 210 is driven by a servo motor 212 dependent from the housing 182. Viewing FIG. 6, rightward movement of the ram member 204 results in a pusher portion 214 of the ram member engaging the first carrier member 16 in que 14 to move this carrier member to the reference position 186. When the ram member 204 is retracted to the position seen in FIG. 3, the next carrier member 16 in the stat que 14 may be advanced against the abutment surface 116 by operation of the stat advancer 108, recalling the description of FIG. 5.

In order to provide means for advancing the sample carrier members 16 from the reference position 186 into and along the loading chute 22 defined by groove 184 in housing 182, a multi-function forward advancer, referenced with the numeral 220, and a portion of which is seen in FIG. 3, but which is best seen in FIG. 7, is associated with the actuator assembly 180. Because of the similarity of the forward advancer 220 with the advancers seen in FIGS. 4 and 5, features of the advancer 220 which are analogous in structure or function with those described earlier are referenced on the advancer 220 with the same numerals used previously, but having a double prime added thereto. Viewing FIG. 7, it is seen that the forward advancer 220 includes a frame 130", with base plate 132" supporting end plates 134", 136", slide shafts 138", and lead screw 140". A servo motor 142" drives the lead screw 140" via a drive assembly 144" and moves a slide block 156" along the slide shafts 138" by action of a nut member 154" threadably engaging the lead screw 140". The one end plate 136" slidably supports a push rod 222 which is drivingly carried by the slide block 156". At its forward end the push rod 222 carries a pusher pad 224, which is visible in FIG. 3 immediately aft of the reference position 186.

Figure 6:
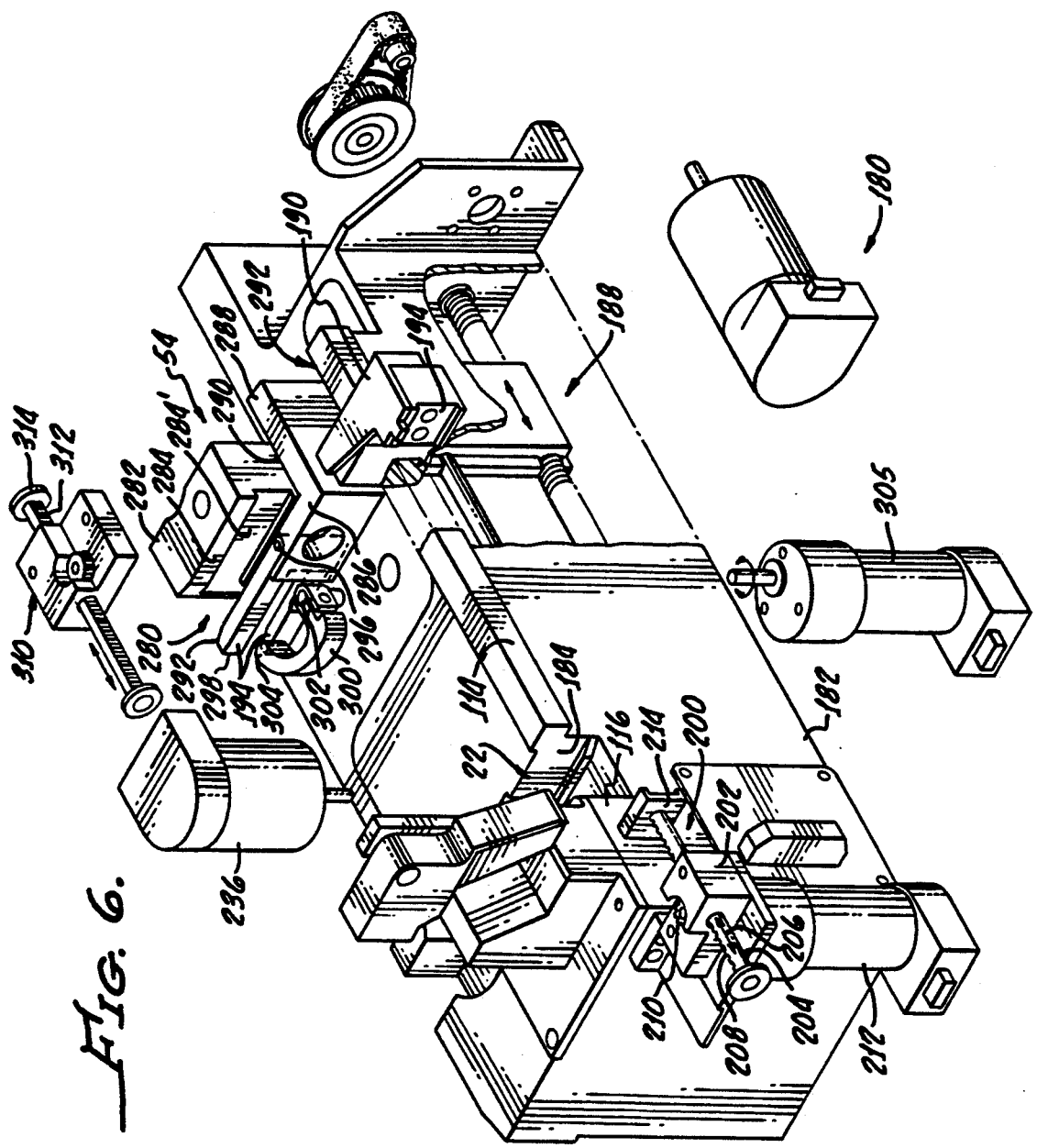
FIG. 6 is a perspective view, partially exploded to better show details of construction, and rendered at a size comparable to that of FIGS. 4 and 5, of a portion of the conveyor apparatus seen in the preceding Figs.

In a first incremental phase of movement, the forward advancer 220 moves pusher pad 224 from the position depicted with dashed lines and referenced with numeral 224' in FIG. 3 forwardly to engage the carrier member 16 at reference position 186, and to slide this carrier member into and along the loading chute defined by groove 184 of the housing 182, recalling actuator assembly 180 seen in FIG. 6. In the case of carrier members from the rank and file on-loading area 12, which are interlocked, this forward movement of the carrier member from reference position 186 has the effect of unlocking it from its neighboring carrier member. The neighboring carrier member is prevented from forward movement by its engagement with the abutment wall 114. The forward advancer 220 moves the carrier from reference position 186 forwardly onto a rotatable turntable member 226 disposed in and forming a portion of the floor 228 of the groove 184 in actuator 180. When the pusher pad 224 reaches a position of forward movement aligning the carrier member 16 with the center of the turntable member 226, the pusher pad 224 is stopped and retracted slightly to be clear of the turntable member 226. This advance-stop-and-retract movement of the pusher pad 224 is indicated on FIG. 3 by the hooked arrow 230 including a reference line 232 indicative of the forward limit of the first increment of advancing of the forward advancer 220.

Once the carrier member 16 is generally centered on the turntable member 226, and the pusher pad 224 is retracted slightly, as was indicated by arrow 230, the actuator assembly 180 rotates the turntable member 226 to spin the sample carrier thereon in front of a bar code reader 234. This rotation of the sample carrier on turntable 226 allows for the reader 234 to read the bar code tag 30 on the sample tube 28 in the carrier 16 regardless of where this tag may be situated on the side of the sample tube. The actuator assembly 180 includes a servo motor 236 which rotates the turntable member 226, and which can position the turntable member and carrier member thereon in increments of one-quarter turn with reference to the position of the turntable and carrier at the start of rotation. Because the rotational orientation of the carrier member may be either of two possible orientations if the carrier member originated on the rank and file area 12, or any of four possible positions if the carrier was placed into the stat que (recalling that stat samples in carriers 16 may be placed into the stat que 14 individually in any orientation), these rotational possibilities for each carrier member 16 were read by the sensors 24 referenced earlier as part of the actuator assembly 180, and are used to cause the turntable member 226 to be stopped with the carrier member 16 thereon in a preferred rotational presentation for further movement along the loading chute 22.

Once the rotational movement of the turntable member 226 is stopped, and the carrier member thereon is presented in the preferred rotational orientation, the forward advancer 220 in a second phase of advancing movement once again advances the pusher pad 224 from the slightly retracted position referenced above with the hooked arrow 230. This second phase of advancement of the pusher pad 224 engages the carrier member on turntable member 226 and moves it along and out of the loading chute 22. As is seen on FIG. 3, the loop conveyor 34 has stopped with an identified receptacle 32 thereof in alignment with the loading chute 22 to receive the carrier member 16.

Loop Conveyor Apparatus and Method

Viewing FIGS. 8 and 9 in conjunction, it will be seen that the loop conveyor 34 includes a frame 240 on which is rotatably carried a pair of spaced apart rotational sprockets 242,244. The sprocket 242 is driven by a servo motor 246, while the sprocket 244 is an idler with provision for adjustment toward and away from the driven sprocket 242. On the sprockets 242,244 circulates a multi-link chain 248. The links of this chain 248 carry plural spaced apart receptacles 32. Thus, an endless train of the receptacles is provided on conveyor 34, which may circulate in either direction and stop with any chosen receptacle in alignment with the on-load chute 22, or with any transfer station 48, or with an off-load station 52 yet to be described in detail. Viewing FIG. 8 in particular it is seen that the receptacles 32 are carried by chain 248 closely past the end of loading chute 22. That is, the floor 228 of the groove 184 in housing 182 which defines the loading chute 22 aligns horizontally with a floor portion 250 of the receptacles 32. Consequently, when the carrier member 16 (seen in phantom lines in FIG. 8) is discharged from the loading chute by pusher member 224 of the actuator assembly 180 during its second phase of forward motion, the carrier is nested into a receptacle 32 on the chain 248 of the loop conveyor 34. As part of its tracking function, the dynamic controller "C" correlates the identification information collected at the bar code reader 234 with the particular one of the receptacles 32 into which a particular sample carrier 16 is placed. So long as the particular sample carrier 16 remains in that particular receptacle, the controller "C", can bring the conveyor 34 to any one of the analyzers 40, for example for transfer of the sample to that analyzer. As each sample carrier 16 is transferred to and from the loop conveyor 34, the controller "C", tracks the samples so that test results can be correlated with particular samples on the conveyor 34.

Consideration of FIG. 8 in additional detail will show that each of the receptacles 32 includes a pair of upright side walls 252,254, and a rear abutment lip 256. Because the abutment lip 256 is relatively short, the back of the receptacles 32 is substantially open so the unloading transfer rams 48 can access the carriers to move them out of the receptacles when desired, recalling the overview of the conveyor 10 provided above. One of the side walls 252 of the receptacles 32 is a bluff wall, while the other side wall 254 includes a resilient finger-like detent member 258. As the carrier members 16 are moved into or out of the receptacles 32, the detent members yield to allow this driven movement. However, the detent members otherwise engage into the notches 78 of the carriers (recalling the description of FIGS. 2A and 28) to positively retain the carriers 16 in the receptacles 32. Thus, the preferred presentation for carrier members exiting the turntable member 226 for introduction into one of the like receptacles 32 is the rotational presentation which places tongue feature 72 toward wall 254. Although various carrier members 16 may be received onto the turntable member 226 in either one of two, or in any one of four rotational positions dependent on whether they are a rank and file carrier or originated with the stat que 14, as described above, all carrier members exit the turntable 226 with the same preferred rotational orientation for their insertion into the receptacles 32 of the loop conveyor 34.

Associated with the loop conveyor in the exemplary embodiment of the invention is a pair of transfer ram assemblies 48, 48' viewing FIG. 9. Each of these transfer ram assemblies is substantially the same so that description of one will suffice to describe both. Also, the transfer ram assembly 48 services analyzer 40, recalling the overview provided above, while the conveyor 10 may service a plurality of such analyzers. Thus, it will be understood that the loop conveyor 34 may include a like plurality of such transfer ram assemblies, each servicing an analyzer 40 and aligned with a receptacle 32 of the chain 248 when this chain stops at the loading chute 22 to receive a carrier member 16 into one of the receptacles thereon. Further, because the transfer ram assembly 48 is similar to the rack and pinion lateral advancer 200 described with reference to FIG. 6, the same reference numerals used previously, but having a prime added thereto, will be used to reference features of the transfer ram assembly 48 which are analogous in structure or function to those features described above.

The transfer ram assembly 48 includes a bridge member 270 spanning the frame 240 of loop conveyor 34. Mounted to the bridge member 270 is a guide block 200', in which a ram member 204' with rack gear teeth 208' is reciprocable (as indicated by arrow 206'). The bridge member 270 also carries a servo motor 212' driving a pinion gear 210' in engagement with the rack gear teeth 208'. A pusher member portion 214' is carried at one end of the ram member 204' and is engageable with the carrier members 16 in receptacles 32 on chain 248. That is, the ram member enters the receptacles 32 between the side walls 252,254 thereof and above the abutment lip 256 to engage the carrier member 16 therein and positively drive this carrier member out of the receptacle. Recalling the over view provided above, the carrier member 16 may be delivered by transfer ram 48 onto the transfer carousel 42 of an analyzer 40, for example.

Alternatively, the transfer assemblies 48 may include a magnetic body which interacts with magnetic features embedded in the carrier 16 themselves, recalling the alternative structures for these carriers which was described above. This magnetic body of the transfer assemblies could then move the carriers 16 by magnetic attraction and a pulling motion rather than the pushing motion described above.

Off-Loading and Interlinking Apparatus and Method

Recalling the over view explanations provided above, and viewing FIGS. 3,6, and 9, it will be seen that the transfer ram assembly 48' of the loop conveyor 34 forms part of the off-loading station 52. The actuator assembly (FIGS. 3 and 6) defines the L-shaped off loading chute, which was referenced generally with the numeral 54 on FIG. 3. This off-loading chute 54 includes a first or entrance leg, referenced with the numeral 280, which is opposite and in alignment with the ram 204 of transfer ram assembly 48'. When the chain 248 of loop conveyor 34 stops with a receptacle 32 opposite the entrance leg 280, and this receptacle contains a carrier member 16 which has been released from the possibility of further testing of the identified contents of the sample tube in this carrier member in one of the analyzers 40, then the ram 204 of the transfer ram assembly 48' is advanced to off load this carrier into the entrance leg 280 of off-loading chute 54.

Consideration of FIG. 6 will show that the entrance leg 280 is defined by the cooperation of an upstanding rectangular boss 282 having a horizontally grooved reference face 284, and one leg 286 of an L-shaped wall 288 also having a reference face 290. The horizontal groove 284' on the face 284 receives the tongue feature 72 of the adjacent side surface 64 of the carrier members 16 so that the side surface itself engages this reference surface. Opposite the reference face 284, a resiliently movable forked guide member 292 having a pair of vertically spaced apart legs 294 is pivotal on an upright pin 296. At its free end 298, the guide member 292 is movable away from the reference face 284 to allow easy entrance of the carrier members 16 from the aligned receptacles 32 of the loop conveyor 34. However, the guide member 292 is also biased toward the reference face 284 so that carrier members 16 are urged into engagement with this reference face at their side surface 64 which defines the tongue feature 72.

Between the spaced apart legs 294 of the guide member 292, an arcuate pusher member 300 is pivotally movable on a drive shaft 302 journaled by the housing 182 of the actuator assembly 180 so that an end 304 of the member 300 sweeps into the entrance leg 280, still viewing FIG. 6. Within the actuator assembly 180, a servo motor 305 is disposed to selectively move the arcuate pusher member 300 between the solid line position seen on FIG. 3, and the dashed line position seen on this Fig. Once a carrier member 16 is delivered into the entrance leg 280 of the off-loading chute 54 by operation of the transfer ram assembly 48', the sweeping motion of the pusher member 300 engages the carrier member with the end surface 304 to move the carrier forwardly and into engagement with the reference surface 290. As will be seen, this forward motion of the carrier member along reference face 284, and into engagement with the reference face 290 has the effect of interlocking the carrier with a previous carrier member to form interlocked ranks of the carriers 16.

Returning for a moment to a consideration of the actuator assembly 180 seen in FIGS. 3 and 6, this assembly is seen to include a dual-stroke rack and pinion type of advancer 310 similar to the transfer ram assemblies 48 already described, and similar to the rack and pinion lateral advancer 200. That is, the advancer 310 included a reciprocable ram 312 with a pusher pad 314 at a forward end thereof which is engageable with the carrier members 16 in the off-loading chute 52. The advancer 310 is effective to move the carrier members 16 individually or as an interlocked rank of carriers incrementally and laterally along a second leg 316 of the off-loading chute 52 in engagement with the reference face 290. The shorter increment of lateral movement effected on the carriers 16 by the advancer 310 is equal the edge dimension of the carriers 16 in plan view. As a result, the successive carrier members are moved incrementally along the second leg 316 of the off-loading chute 52 so that the last carrier in line has its side surface 66 defining groove 74 in alignment with the reference surface 284. When the next successive carrier member 16 is advanced by pusher member 300 along reference surface 284 and into engagement with the reference surface 290, the projecting tongue feature 72 of this carrier member moving along the groove 284' exits this groove to be received into the dove-tailed groove 74 of the preceding carrier member. Thus, succeeding ones of the carrier members 16 are linked together into ranks which extend onto the off-loading tray 56.

Also included on the actuator assembly 180, viewing FIGS. 3 and 6, is a proximity sensor 320 (seen on FIG. 3) which detects when a selected number (six, for example) of the carrier members 16 have been interlinked. When the sensor 320 is triggered by the presence of a carrier member 16, the advancer 310 is caused to advance a large increment of distance (double the edge dimension of the carriers 16) rather than the smaller increment described above. This larger increment of advancement for the advancer 310 moves the rank of interlocked carriers onto the off-loading tray 56 in preparation for the start of another rank of such carriers.

Figure 10:
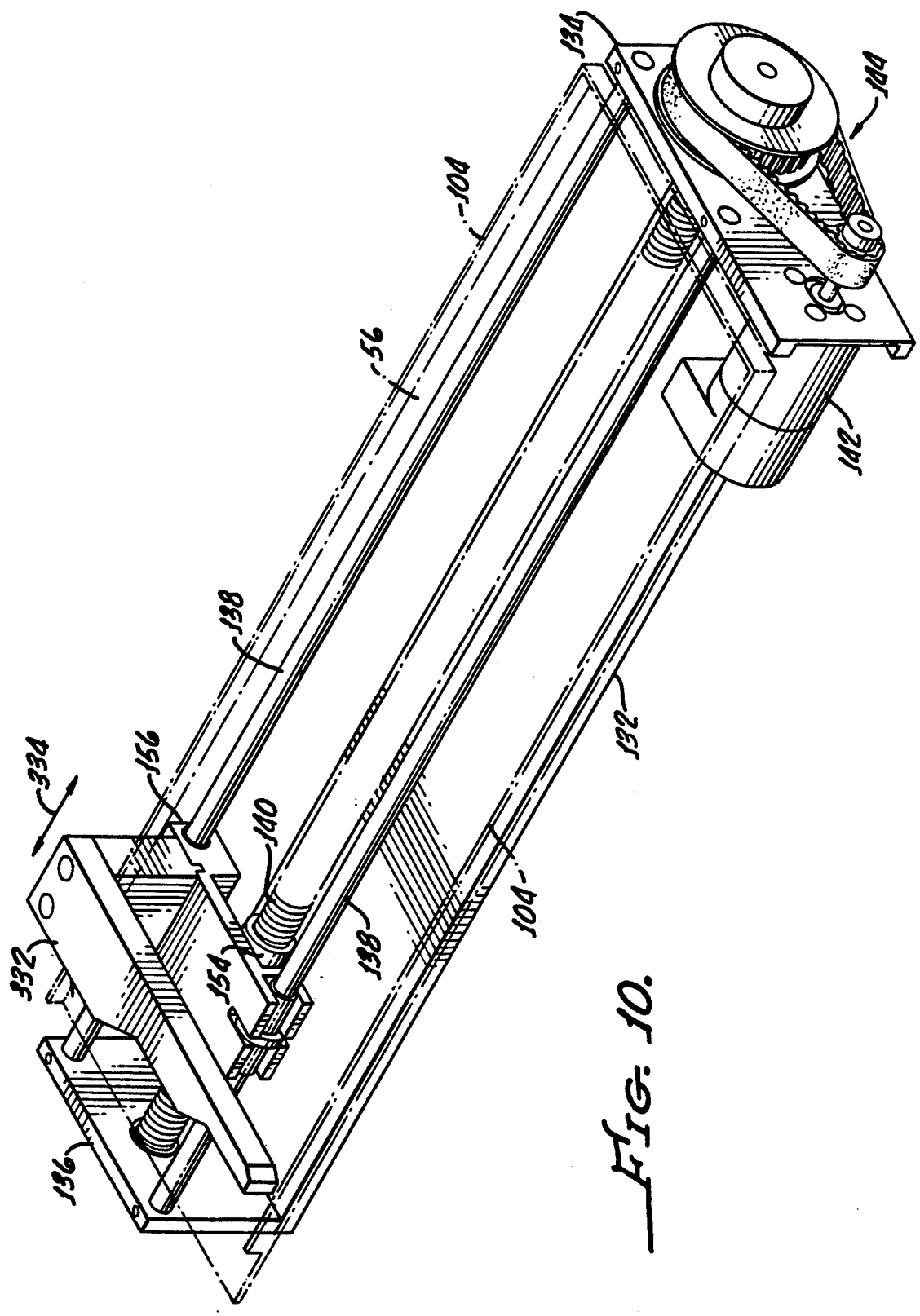
FIG. 10 is a perspective view of yet another portion of the conveyor apparatus partially seen in the other drawing Figs.

In order to move the ranks of interlinked carriers on off-loading tray 56 out of the way of the leg 316 of the off-loading chute 52 so that the next rank of carriers can extend from this chute onto the tray, an off-loading advancer 330 (seen in FIG. 10) is associated with this off-loading tray. The off-loading advancer 330 is disposed below the off-loading tray 56, and includes an arm portion 332 (part of which is seen in FIG. 3) extending across the tray 56 at the forward end thereof to engage the adjacent carrier members 16. Because of its similarity with the advancer assemblies 100,102,188, and 220, described in detail above, the advancer 310 is not further described in detail, and features of this advancer which are similar in structure or function to those described above are referenced on FIG. 10 with numerals (primes not being used on the reference numerals of FIG. 10) which by now will be familiar to the reader. The off-loading advancer 330 strokes the arm portion 332 toward the free end 58 of the off-loading tray 56 after each large-increment movement of the advancer 310, as is indicated by the arrow 334.

Consequently, the rank of interlocked carriers 16 which has most recently been moved onto the off-loading tray 56 is moved toward the free end 58 of this tray until either the edge wall 104 of this tray is encountered or until the other interlocked carrier members already moved to the free end of the off-loading tray 56 are encountered. As a result, the interlocked carrier members 16 are again presented to the attendant personnel for the conveyor 10 as rank and file groups which offer very convenient and easy handling. Upon completion of this advancing movement grouping the interlinked carriers 16 at the free end 58 of the off-loading tray 56, the arm 332 is returned by advancer 330 to its position at the forward end of this tray awaiting formation of the next rank of interlocked carriers.

In view of the above, it is easily seen that the present invention provides apparatus and methods for accepting sample tubes either in individual carriers or in ranks of interlocked carriers; for separating the interlocked carriers from one another; for feeding the individual carriers to an endless loop conveyor transporting the carriers and samples to analysis apparatus; for receiving back from the analysis apparatus tested samples or samples in process of testing, and holding these samples for the next step of processing or for verification of the test results on particular samples; and for off-loading the samples in their carriers and once again linking the carriers into easily handled ranks.

Those ordinarily skilled in the pertinent art will recognize that the controller "C" may employ a number of possible architectures. For example, a relay or solid state logic structure may be used to operate the conveyor 10. Alternatively, a microprocessor-based controller or microcomputer may operate the conveyor. Again alternatively, and preferably, a general purpose computer such as a personal or minicomputer may be programmed to operate the conveyor 10, and to also interface and coordinate operation of the analysis modules 40 with the conveyor 10, as well as to perform other necessary analysis such as receipt and correlation as well as comparison and verification of test results from the analyzers 40.

While the present invention has been depicted, described, and is defined by reference to a single particularly preferred embodiment of the invention, such reference is not intended to imply a limitation on the invention, and no such limitation is to be inferred. The invention is intended to be limited only by the spirit and scope of the appended claims, which also provide a definition of the invention.

What is claimed is:

1. An automated chemical analyzer for conducting selected chemical analysis including plural substantially identical interlinkable prismatic sample carrier members for carrying a plurality of samples, at lease one analysis module portion for analysis of said samples, said carrier members including means for removably interlinking and unlinking said carrier members together side-by-side by lateral relative sliding movement, said analyzer further including conveyor apparatus comprising:

on-loading means for receiving interlinked elongate pluralities of said prismatic sample carriers;

means for unlinking individual sample carriers from said elongate pluralities of interlinked sample carriers;

conveyor means including plural substantially identical receptacles each for receiving an individual sample carrier and conveying said individual sample carrier to said analysis module portion;

means for feeding individual sample carriers into said receptacles;

means for transferring individual sample carriers between said receptacles and said analysis module;

off-loading means for transferring individual sample carriers from said receptacles toward an off-loading area; and interlinking means cooperating with said off-loading means to interlink said sample carriers into elongate pluralities presented on said off-loading area.

2. The invention of claim 1 wherein said on-loading means includes an elongate tray member defining an upper surface upon which said interlinked elongate pluralities of sample carriers are slidably receivable, and first advancer means associated with said tray member for engaging and advancing said interlinked sample carrier pluralities toward said unlinking means.

3. The invention of claim 2 wherein said first advancer means includes a frame journaling an elongate lead screw and carrying a servo motor drivingly connected with said lead screw, a non-rotational nut member threadably engaged on said lead screw and moving longitudinally thereof in response to rotation of said lead screw by said servo motor, said nut member carrying carrier member engagement means for ratcheting engagement of said sample carriers on said tray member.

4. The invention of claim 3 wherein said ratcheting carrier member engagement means includes a pair of spaced apart pivotal drive dog members each movable along a respective side edge of said tray member and pivoting to engage said interlinked elongate pluralities of carrier members in response to movement of said nut member toward said unlinking means, said drive dog members pivoting to ratchet past said interlinked pluralities of carrier members in response to opposite movement of said nut member.

5. The invention of claim 4 wherein said first advancer is situated below said tray member, said drive dog members extending upwardly from below said tray member along a side edge thereof and extending inwardly of said tray member to on the one hand drivingly engage said carrier members and on the other hand to rachet over said carrier members in response to respectively opposite movements of said drive dog members relative to said tray member.

6. The invention of claim 1 wherein said means for unlinking individual sample carriers from said elongate pluralities of sample carriers includes an abutment surface against which said pluralities are engageable, lateral advancer means for advancing an interlinked elongate plurality of carrier members along said abutment wall so that one of said carrier members extends beyond said abutment surface and the next adjacent carrier member engages said abutment surface, and forward advancer means for advancing said one carrier member laterally relative said next adjacent carrier member to thereby unlink the former carrier member from the latter carrier member.

7. The invention of claim 6 wherein said lateral advancer means includes a housing journaling an elongate lead screw and carrying a servo motor drivingly connected with said lead screw, a non-rotational nut member threadably engaged on said lead screw and moving laterally in response to rotation of said lead screw by said servo motor, said nut member driving a pusher member engaging said elongate plurality of carrier members at an end thereof opposite said one carrier member.

8. The invention of claim 7 wherein said forward advancer means includes a frame journaling an elongate lead screw and carrying a servo motor drivingly connected with said lead screw, a non-rotational nut member threadably engaged upon said lead screw and longitudinally movable in response to rotation of said lead screw by said servo motor, said nut member driving an elongate push rod member slidably guided also on said frame, said push rod member at a forward end thereof carrying a pusher pad portion engageable with said one carrier member.

9. The invention of claim 1 wherein said conveyor means includes a frame movably carrying an endless loop flexible member, and a servo motor drivingly connected with said flexible member, said flexible member carrying a regularly spaced plurality of receptacle members upstanding thereon, each of said receptacle members being configured to receive a respective individual sample carrier member.

10. The invention of claim 9 wherein said conveyor means frame carries a transfer ram assembly defining a part of said means for transferring said carrier members between said receptacles and said analysis module, said transfer ram assembly including a guide block reciprocably receiving a ram member, a servo motor selectively reciprocating said ram member, and said ram member carrying a pusher portion at a forward end thereof extensible into said receptacles to push individual sample carrier members therefrom to said analyses module.

11. The invention of claim 10 wherein said conveyor means frame further carries another transfer ram assembly defining a part of said off loading means, said off-loading means further including an off-loading chute having an entrance leg aligned oppositely to said another transfer ram assembly, and said conveyor means disposing a selected one of said receptacles in alignment with said entrance leg to receive a carrier member therefrom.

12. The invention of claim 11 wherein said off-loading chute includes a resilient bifurcated wall member having a spaced apart pair of legs and urging carrier members received into said off-loading chute into engagement with a first reference surface defined opposite to said bifurcated member.

13. The invention of claim 12 wherein said interlinking means includes an arcuate pusher member operable between said legs of said bifurcated member to move said carrier members in said entrance chute therealong.

14. The invention of claim 13 wherein said off-loading chute is L-shaped to define a second reference surface against which said carrier members are moved by said arcuate pusher member, said interlinking means including a dual-function incremental advancer which with a smaller increment of advancement moves a carrier member in engagement with said second abutment surface a distance corresponding to the edge dimension of said carrier members in plan view, whereby the next successive carrier member in said entrance chute is moved along said first reference surface by said arcuate pusher member and laterally relative said preceding carrier member toward said second reference surface to thereby interlink said preceding and said next-successive carrier members.

15. The invention of claim 14 wherein said dual-function incremental advancer with a larger increment of advancing movement advances a completed plurality of said interlinked carrier members out of said off-loading chute and onto an off-loading tray member of said off-loading area.

16. The invention of claim 15 further including an off-loading advancer having an arm portion disposed across said off-loading tray member, said off-loading advancer in response to advancing of a completed interlinked plurality of carrier members onto said off-loading tray member by a larger incremental advancement of said incremental advancer engaging said plurality of carrier members with said arm portion to move said interlinked plurality of carrier members free of said off-loading chute.

17. The invention of claim 8 wherein said means for feeding individual carrier members into said receptacles includes said forward advancer moving said one unlinked carrier member past alignment with said abutment surface and along a loading chute aligned with a receptacle of said conveyor means.

18. The invention of claim 17 further including sensor means for sensing a rotational orientation of said one unlinked carrier member, and rotator means for rotating said one unlinked carrier member in a horizontal plane to a preferred orientation for receipt into said receptacle.

19. The invention of claim 18 wherein said rotator means includes a turntable defining a portion of a floor surface of said loading chute, and means for rotating said turntable.

20. The invention of claim 1 wherein said prismatic sample carriers each have a body which defines a generally square shape in plan view and a rectangular shape in elevation view with an upwardly opening central cavity for receiving a respective sample, said sample carriers each defining like pairs of opposed side surfaces one pair of which defines respective ones of an interlinkable horizontal dove-tail tongue and groove feature, and the other pair of opposed side surfaces defining a horizontal tongue and groove feature which mutually supports adjacent interlinked elongate pluralities of such carriers when mutually engaged.

21. The invention of claim 20 wherein said carrier members further include detent means for retaining said carrier members in interlinked engagement one with another.

22. The invention of claim 21 wherein said detent means includes said dove-tail tongue feature including a vertical notch, and said carrier member including a resilient detent member projecting outwardly in said dove-tail groove feature and receivable into said vertical notch to removably detent said carriers in interlinked relationship.

23. The invention of claim 22 wherein said receptacles of said conveyor means include a pair of spaced apart walls with a floor extending therebetween and onto which said carrier members are slidable, an abutment lip extending between said pair of walls at one side thereof, and an open side defined between said pair of walls opposite said abutment lip.

24. The invention of claim 23 wherein one of said pair of walls of said receptacle includes an upright resilient finger portion receivable into said vertical notch of said carrier member feature to retain said carrier members within said receptacles.

25. The invention of claim 18 further including identifier means associating with said rotator means to read an identification indicia associated with said sample within each individual sample carrier.

26. The invention of claim 19 wherein said identification indicia includes a bar code tag, and said identifier means includes a bar code reader.

27. The invention of claim 1 further including second on-loading means for receiving individual sample carriers.

28. The invention of claim 27 wherein said second on-loading means includes a respective second elongate tray member slidably receiving a single que of said sample carriers, and a respective second advancer associated with said second tray member for engaging and advancing said single que of sample carriers thereon.

29. The invention of claim 28 wherein said second advancer includes a frame journaling an elongate lead screw and carrying a servo motor drivingly connected with said lead screw, a non-rotational nut member threadably engaging said lead screw and moving longitudinally thereof in response to rotation of said lead screw by said servo motor, said nut member driving carrier member engaging means for ratcheting engagement with said sample carriers on said second tray member.

30. The invention of claim 29 wherein said apparatus further includes a lateral advancer for engagement with a first carrier member in said single que of carrier members to move said first carrier member laterally to said means for feeding said individual carriers to said receptacles.

31. The invention of claim 30 wherein said lateral advancer includes a guide block reciprocably receiving a ram member, a servo motor selectively reciprocating said ram member, and said ram member carrying a pusher portion at a forward end thereof engageable with said first carrier member of said single que of carrier members.

* * * * *